United States Patent
Shi et al.

(10) Patent No.: US 11,766,201 B2
(45) Date of Patent: Sep. 26, 2023

(54) LANCING DEVICE WITH REAR ADJUSTMENT OF PENETRATION DEPTH

(71) Applicant: STERILANCE MEDICAL (SUZHOU) INC., Jiangsu (CN)

(72) Inventors: Guoping Shi, Suzhou (CN); Anthony Scott Horstman, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 778 days.

(21) Appl. No.: 16/758,531

(22) PCT Filed: Oct. 23, 2018

(86) PCT No.: PCT/CN2018/111339
§ 371 (c)(1),
(2) Date: Apr. 23, 2020

(87) PCT Pub. No.: WO2019/080823
PCT Pub. Date: May 2, 2019

(65) Prior Publication Data
US 2020/0253523 A1    Aug. 13, 2020

(30) Foreign Application Priority Data
Oct. 23, 2017    (CN) .......................... 201710992710.0

(51) Int. Cl.
*A61B 5/15*    (2006.01)
*A61B 5/151*    (2006.01)
(52) U.S. Cl.
CPC ........ *A61B 5/150183* (2013.01); *A61B 5/151* (2013.01); *A61B 5/15111* (2013.01); *A61B 5/150198* (2013.01)

(58) Field of Classification Search
CPC .......... A61B 5/150198; A61B 5/15019; A61B 5/150412; A61B 5/15113; A61B 5/15117; A61B 5/1513
See application file for complete search history.

(56) References Cited

U.S. PATENT DOCUMENTS

| 5,613,978 A | 3/1997 | Harding |
| 2007/0083222 A1* | 4/2007 | Schraga ........... A61B 5/150183 |
| | | 606/181 |

(Continued)

FOREIGN PATENT DOCUMENTS

| CN | 202891945 U | 4/2013 |
| CN | 107638180 A | 1/2018 |
| CN | 107854129 A | 3/2018 |

OTHER PUBLICATIONS

Apr. 30, 2019 Search Report issued in International Patent Application No. PCT/CN2018/111339.

*Primary Examiner* — Devin B Henson
*Assistant Examiner* — H. Q. Nguyen
(74) *Attorney, Agent, or Firm* — Oliff PLC

(57) ABSTRACT

A lancing device with rear adjustment of penetration depth includes a cap, cap holder, ejection pin and shell, wherein: the lancing device has an external and medium depth adjusting sleeve. The ejection pin is located in the medium sleeve and the external depth adjusting sleeve is sleeved outside the medium sleeve; the external sleeve connects axially and circumferentially to the shell, and a rotary locating mechanism is between the external sleeve and the shell; the medium sleeve is connected circumferentially and axially in a sliding way, and a rotary moving mechanism is between the medium the external sleeve, and the medium includes a passive impact face relative to the active impact face of the ejection pin; the external sleeve includes a manual adjusting ring outside the lancing device at the (Continued)

middle and rear part, and rotates to drive the medium sleeve to move axially, changing the needle tip penetration depth.

9 Claims, 13 Drawing Sheets

(56) References Cited

U.S. PATENT DOCUMENTS

| | | | |
|---|---|---|---|
| 2008/0027474 A1* | 1/2008 | Curry | A61B 5/150519 606/181 |
| 2010/0049234 A1* | 2/2010 | Kitamura | A61B 5/1519 606/182 |
| 2010/0241149 A1* | 9/2010 | Nishiyama | A61B 5/150412 606/181 |

* cited by examiner

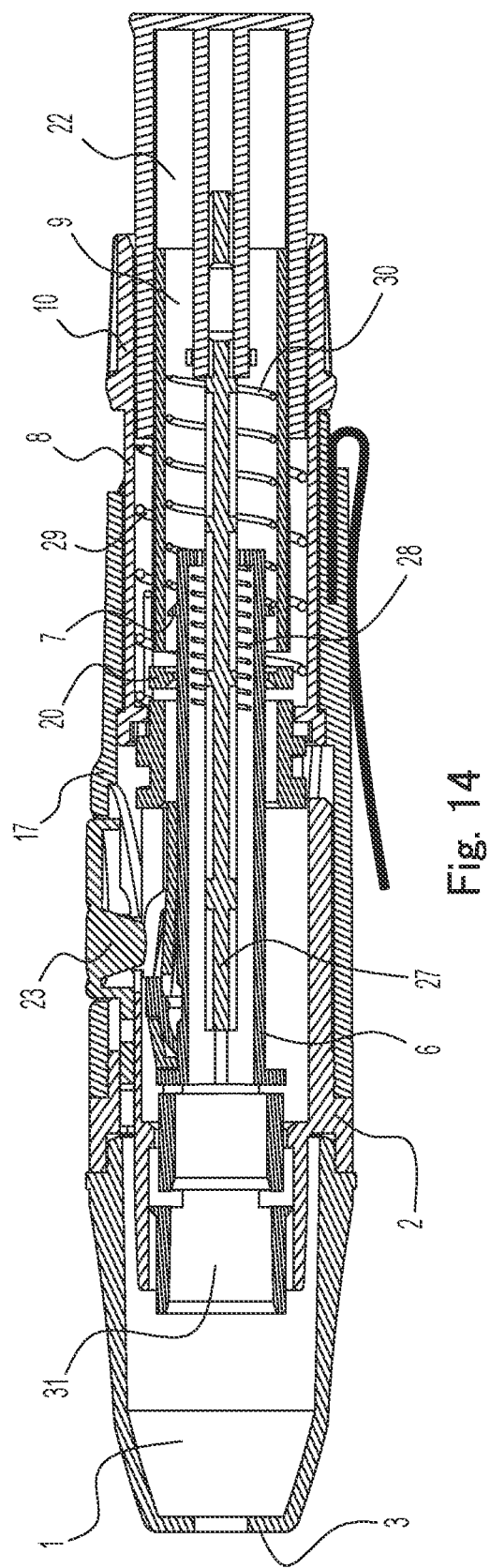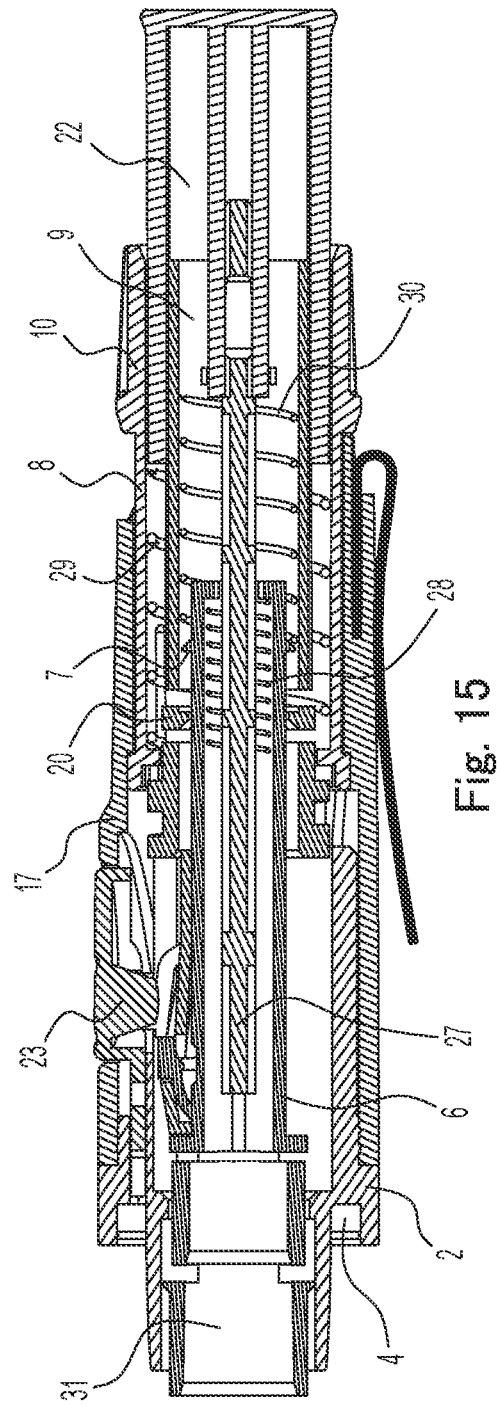

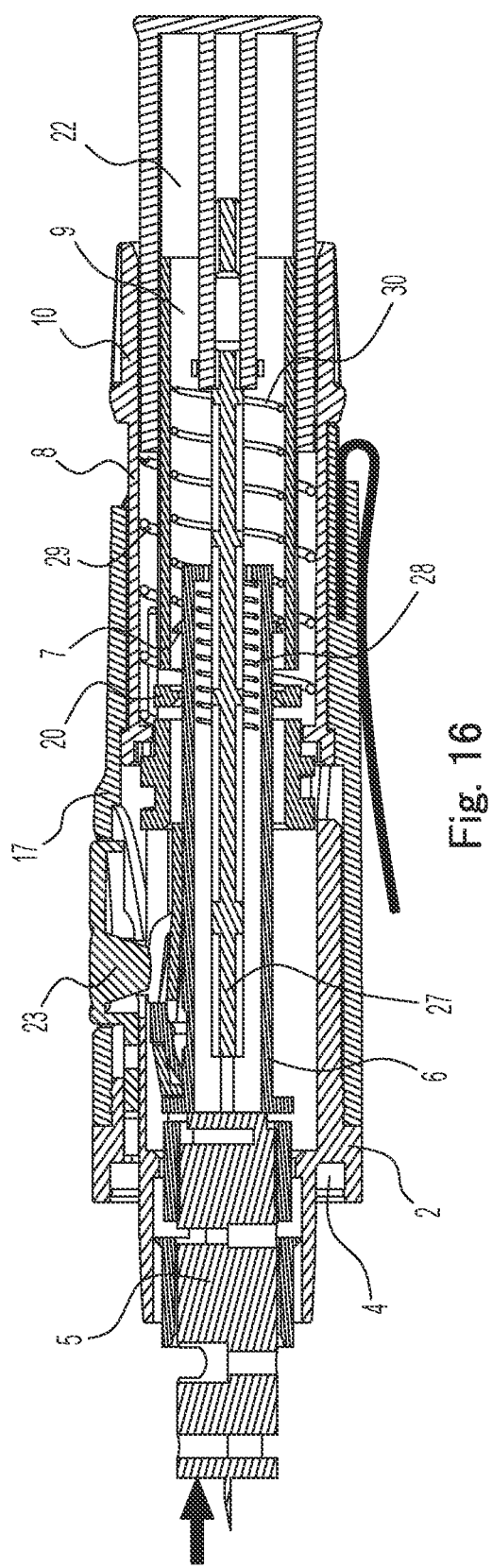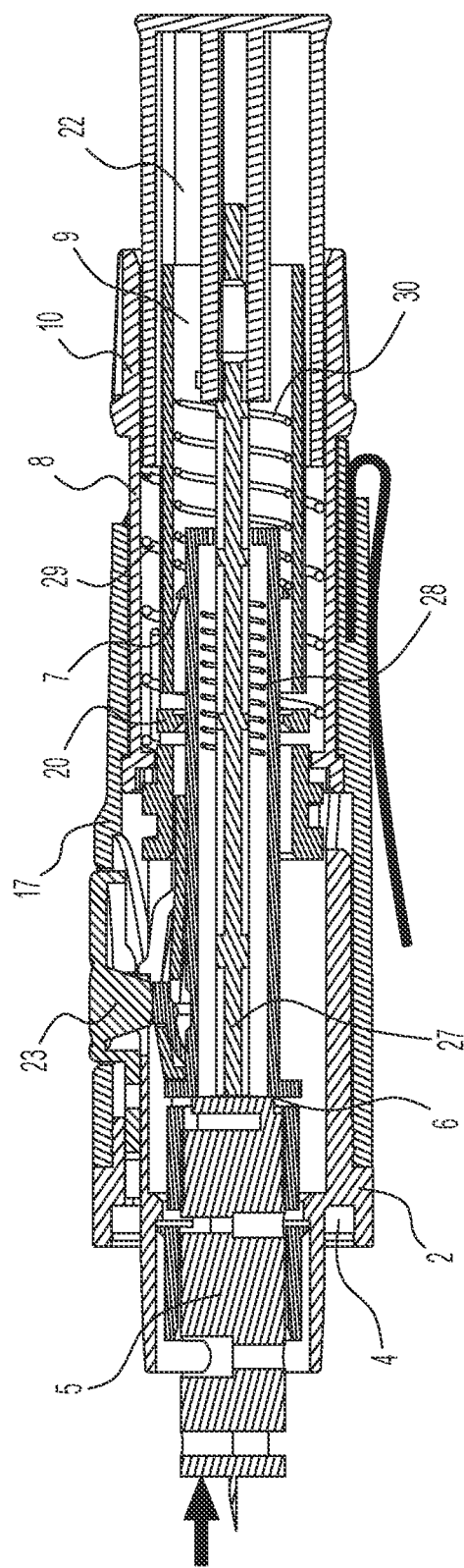

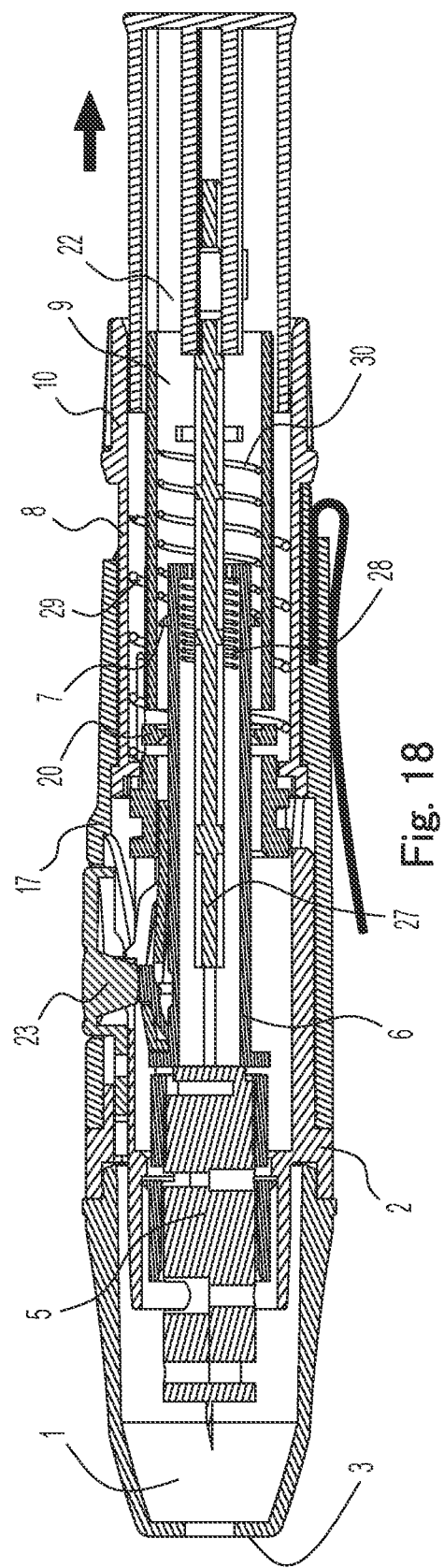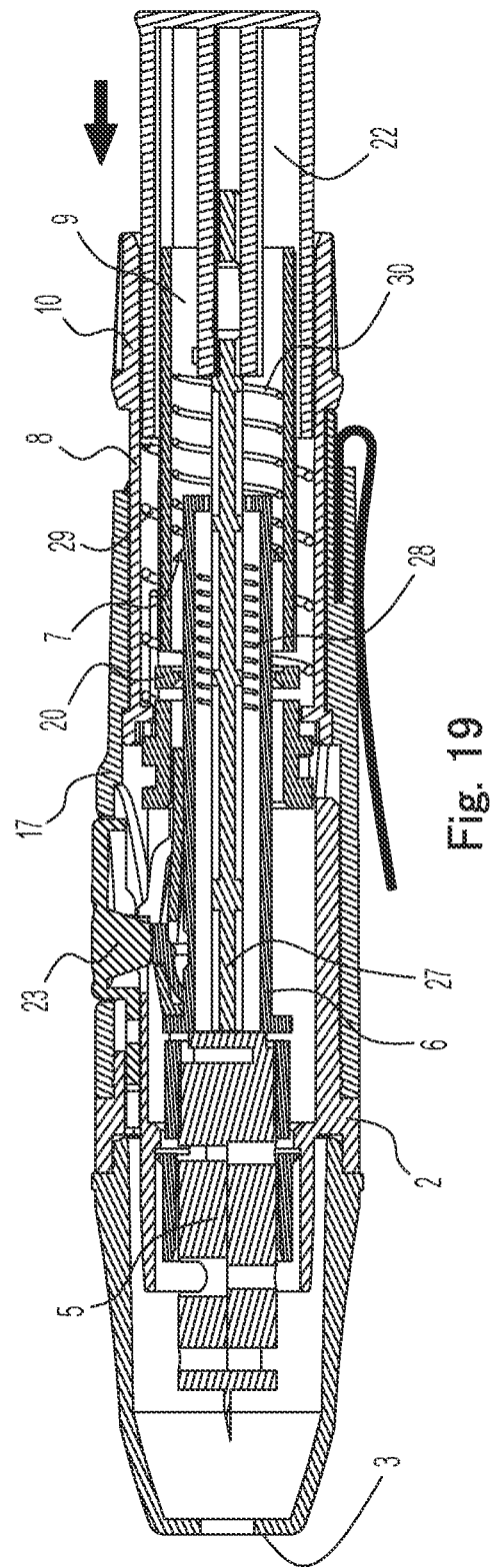

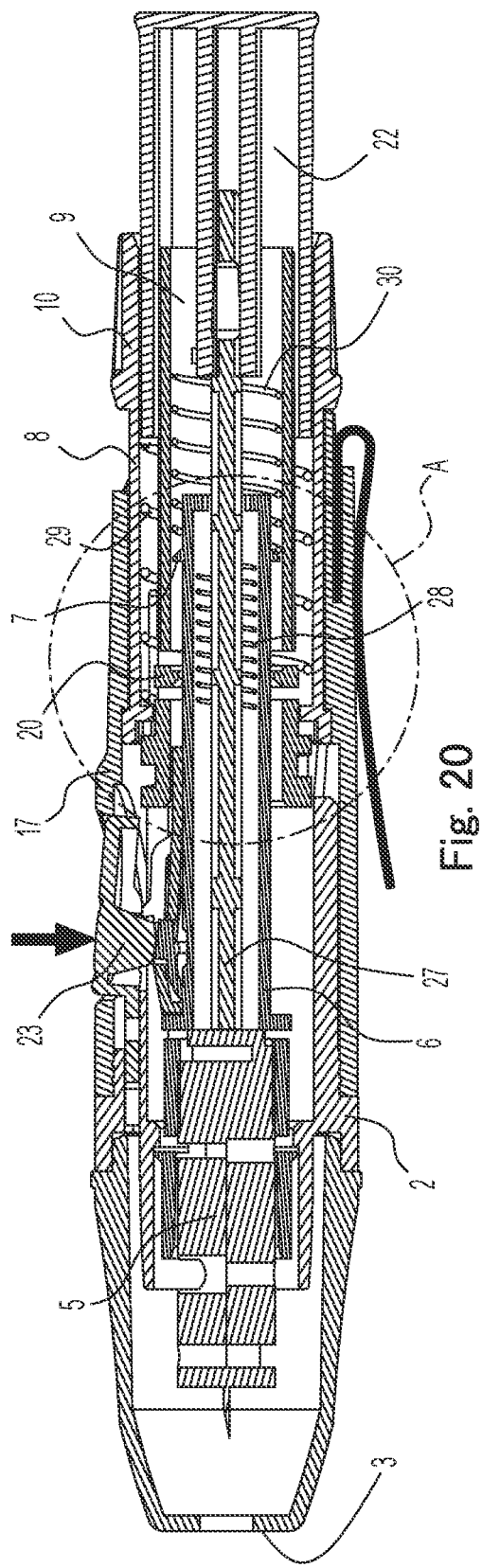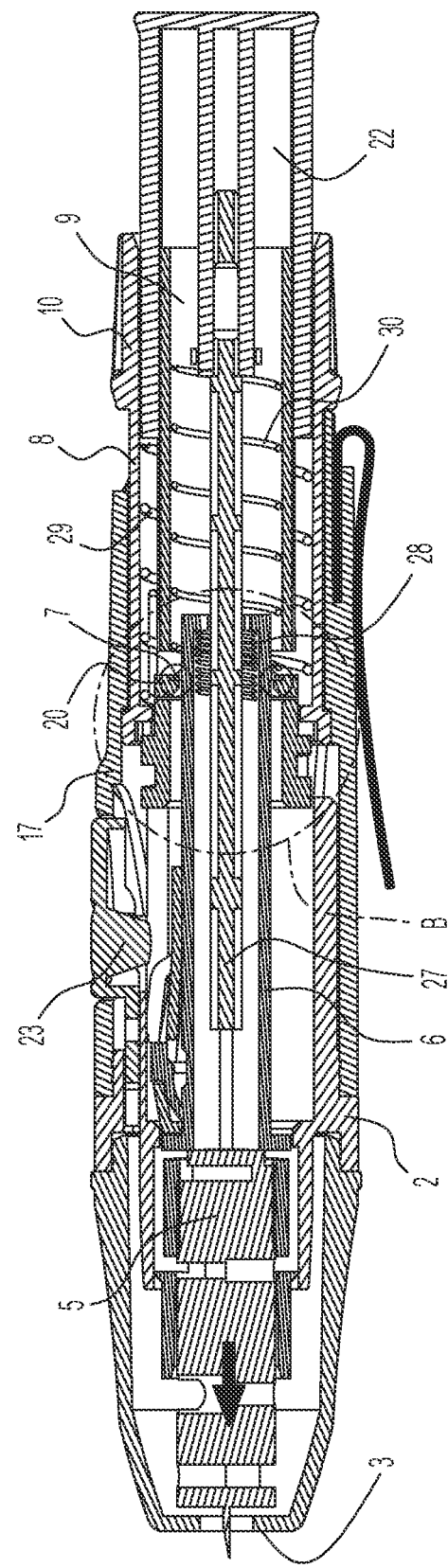

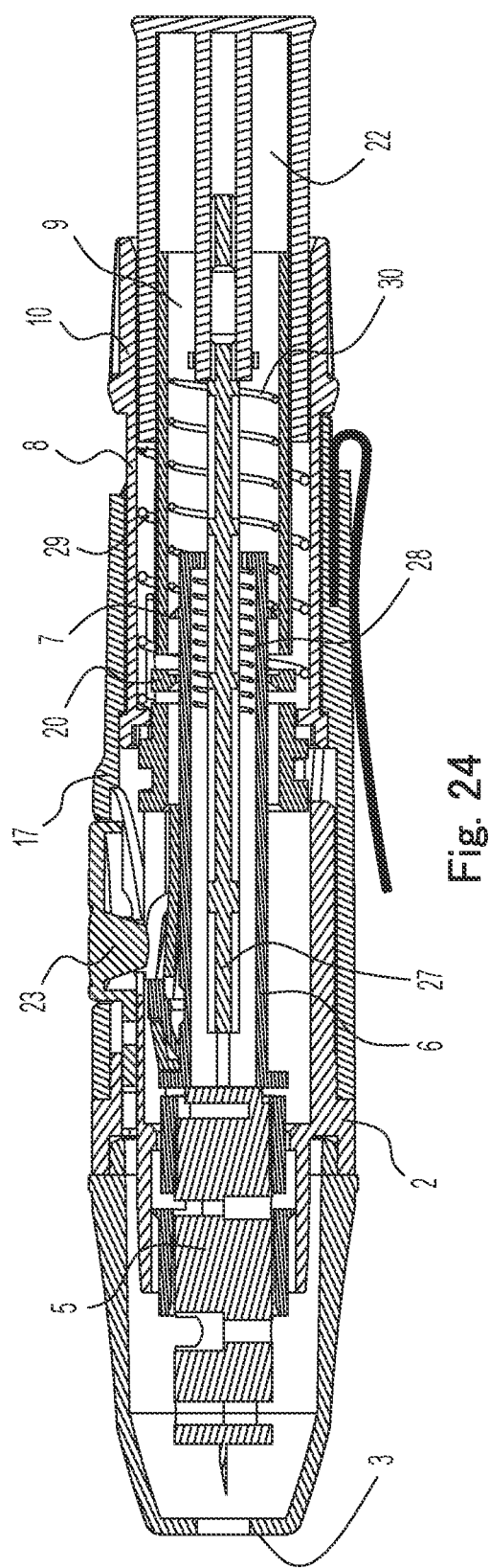
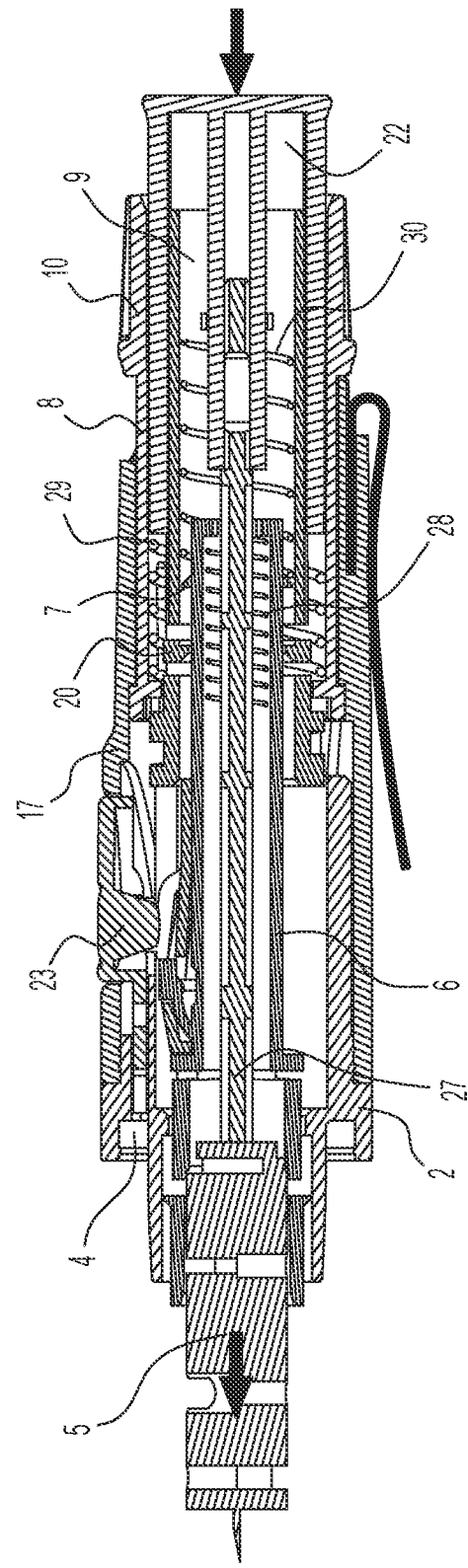
Fig. 24
Fig. 25

LANCING DEVICE WITH REAR ADJUSTMENT OF PENETRATION DEPTH

TECHNICAL FIELD

The present invention relates to the medical lancing device, especially relates to a lancing device used with the disposable lancet. The lancing device has the characteristic of rear adjustment of penetration depth.

BACKGROUND OF INVENTION

The lancing device is a blood sampling device used with the disposable lancet wherein the lancing device could be used repeatedly, but the lancet is disposable in order to avoid the cross infection. The lancing device has been developed for several decades, and the lancing device has been improved many times and it's becoming mature, and during the development of lancing device, the lancing device is designed with penetration depth adjustment mechanism to meet the demands of different blood sampling subjects of different age (such as adults and children) and different skin thickness.

On Apr. 24, 2013, Chinese Patent CN202891945U announced and authorized a utility model patent with the patent number of 2012204829392 and the title of <Painless Lancing Device>. The patent is designed with a penetration depth adjustment mechanism, and the adjusting component is an adjusting tip, which is arranged at the front of the lancing device.

On Mar. 25, 1997, U.S. Pat. No. 5,613,978 announced and authorized an invention patent with the title of <Adjustable tip for lancet device>. The patent is also designed with a penetration depth adjustment mechanism, and the adjusting component is an adjusting tip, which is arranged at the front of the lancing device.

Although the above two patent cases have provided the technical solutions to adjust the penetration depth, the adjusting components (adjustment tips) are both arranged on the caps at the front of the lancing device, which could change the adjusted penetration depth by mistake as it's necessary to dismount the adjustment tip during the installation of lancet in the actual use process. Especially for the individual use by diabetic patients, the penetration depth is generally not changed after it is determined, and the individual users don't expect to change the penetration depth by mistake in the future use (during installation of the lancet).

Therefore, it's the research subject of the present invention to solve the above problem and design a better penetration depth adjustment mechanism to eliminate the interference.

DISCLOSURE OF THE INVENTION

The present invention provides a lancing device with rear adjustment of penetration depth with the purpose to solve the problem that the installation of the lancet on the lancing device interferes with the penetration depth described in the background of invention.

In order to achieve the above purpose, the technical solution adopted by the present invention is: a lancing device with rear adjustment of penetration depth comprises a cap, a cap holder, an ejection pin and a shell, wherein:

The cap is a sleeve type cap at the head of the lancing device, and the cap is provided with a lancing end face to contact the lancing site of human body at its front end.

The cap holder is the base used to connect and fit with the cap at the front of the lancing device, and the cap and the cap holder are fit and connected through the connection port.

The ejection pin is an ejection component capable of mounting a lancet, and the ejection pin or the lancet is provided with an active impact face.

The shell is the shell of the lancing device, and the shell and the cap holder are fixedly connected, or the shell and the cap holder are an integrative structure.

Wherein: the lancing device is provided with an external depth adjusting sleeve and a medium depth adjusting sleeve. The main bodies of the external depth adjusting sleeve and the medium depth adjusting sleeve are sleeve structures. The ejection pin is located in the medium depth adjusting sleeve and the external depth adjusting sleeve is sleeved outside the medium depth adjusting sleeve.

The external depth adjusting sleeve is connected in the circumferential direction of the lancing device relative to the shell in a rotational way and it's connected in the axial direction of the lancing device in a locating way; the external depth adjusting sleeve is provided with a manual adjusting ring, and the manual adjusting ring is a sleeve at the middle and rear of the external depth adjusting sleeve, and in the assembly state, the manual adjusting ring is exposed at the middle outside or rear outside of the lancing device, so that the user can rotate and adjust manually; between the external depth adjusting sleeve and the cap holder or shell, one is provided with a rotary locating slot, and the other is provided with a rotary locating block, and the rotary locating slots are several slots spaced on the circumferential direction of the lancing device, and the rotary locating blocks are blocks configured for the corresponding rotary locating slots, and the matching between the rotary locating slots and rotary locating blocks forms a rotary locating mechanism of the external depth adjusting sleeve in the circumferential direction of the lancing device relative to the shell.

The medium depth adjusting sleeve is connected in the circumferential direction of the lancing device relative to the shell in a locating way and it's connected in the axial direction of the lancing device in a sliding way; the medium depth adjusting sleeve is provided with a passive impact face relative to the active impact face; between the medium depth adjusting sleeve and the external depth adjusting sleeve, one is provided with a spiral groove and the other is provided with a drive block, and the drive block is a block configured for the corresponding spiral groove, and the matching of the spiral groove and the drive block forms a moving mechanism of the medium depth adjusting sleeve in the axial direction of the lancing device relative to the shell.

In the assembly state, rotate the manual adjusting ring on the external depth adjusting sleeve to drive the medium depth adjusting sleeve to move axially relative to the shell of the lancing device, so as to change the distance between the lancing end face and the passive impact face in the axial direction of the lancing device, so as to adjust the penetration depth of the needle tip.

The above described technical solution is explained as follows:

1. In above described technical solution, the "front" in mentioned "front end" and "forward" refers to direction pointed by the tip of lancing device or ejection direction of lancet. The "rear" in mentioned "rear end" and "rearward" refers to the direction pointed by the tail of lancing device or the opposite direction of ejection of lancet.

2. In above described technical solution, the "axial direction" refers to axial direction of the lancing device, i.e.

the ejection direction connected from the tip to the tail of lancing device or anteroposterior direction. The "circumferential direction" refers to the peripheral direction of the lancing device.

3. In above described technical solution, the medium depth adjusting sleeve is provided with an inner lug on the inner wall, and the passive impact face is the end face of the inner lug against the active impact face. The active impact face is arranged on the side of the ejection pin or the lancet (5) corresponding to the motion path of the passive impact face.

4. In above described technical solution, the medium depth adjusting sleeve is a tubular member, and the tubular member is provided with at least two pairs of division slots at its outer edge along the transverse direction of the tubular body, and each pair of division slots is formed by the two slots spaced in the axial direction of the tubular body, and all pairs of division slots are spaced along the circumferential direction at the outer edge of the medium depth adjusting sleeve, and the opening of the slots in the circumferential direction at the outer edge of the medium depth adjusting sleeve is less than 180 degrees and the slots are on the tube walls through the medium depth adjusting sleeve in the radial direction of the tubular body, and each pair of division slots isolates the tube wall in the middle to be an elastic bridge, and the two ends of the elastic bridge are integrated with the medium depth adjusting sleeve, the arch of the elastic bridge is independent relative to the medium depth adjusting sleeve and the passive impact face is arranged on the arch or the arch extension, and it's on the lateral side where the arch or the arch extension is against the active impact face to form the buffer structure of elastic bridge. In the buffer structure of elastic bridge, the arch extension has the following two forms:

The first form is that the arch extension is an inner lug extending inward from the inner side of the arch and the passive impact face is the lateral face where the inner lug is against the active impact face, so the active impact face cooperates with the passive impact face in the inner side of the medium depth adjusting sleeve in an impact way.

The second form is that the arch extension is an outer lug extending outward from the outer side of the arch and the passive impact face is the lateral face where the outer lug is against the active impact face, so the active impact face cooperates with the passive impact face in the outer side of the medium depth adjusting sleeve in an impact way.

The design principle and technical conception of the present invention are as follows: in order to solve the existing problem of the installation of the lancet interfering with the penetration depth, the present invention separates the penetration depth adjusting mechanism from the head of the lancing device and moves it to the middle or rear part of the lancing device. At this time, in order not to affect the basic structure and layout of the original design of the lancing device, while considering the rationality, simplicity and process manufacturability of the structural design, the lancing device is designed with an external depth adjusting sleeve and a medium depth adjusting sleeve, and the ejection pin is arranged in the medium depth adjusting sleeve and the external depth adjusting sleeve is sleeved outside the medium depth adjusting sleeve, wherein the external depth adjusting sleeve is connected in the circumferential direction of the lancing device relative to the shell in a rotational way and it's connected in the axial direction of the lancing device in a locating way, and the external depth adjusting sleeve is provided with a manual adjusting ring, and in the assembly state, the manual adjusting ring is exposed at the middle outside or rear outside of the lancing device, so that the user can rotate and adjust manually, and a rotary locating mechanism is arranged between the external depth adjusting sleeve and the cap holder or the shell; the medium depth adjusting sleeve is connected in the circumferential direction of the lancing device relative to the shell in a locating way and it's connected in the axial direction of the lancing device in a sliding way, and a moving mechanism by the matching of the spiral groove and the drive block between the medium depth adjusting sleeve and the external depth adjusting sleeve, and the medium depth adjusting sleeve is provided with a passive impact face corresponding to the active impact face of the ejection pin or the lancet, and in the assembly state, rotate the manual adjusting ring to drive the medium depth adjusting sleeve to move axially relative to the shell, so as to change the distance between the lancing end face and the passive impact face in the axial direction of the lancing device, so as to adjust the penetration depth of the needle tip.

Due to the application of the above described solution, the present invention has the following advantages and effect in comparison with the prior art:

1. In terms of function, the present invention can effectively separate the penetration depth adjusting mechanism from the head of the lancing device and move it to the middle or rear part of the lancing device, so as to completely solve the problem of the installation of the lancet interfering with the penetration depth.

2. On the premise of keeping the original basic structure and design layout of the lancing device, the invention reasonably and effectively solves the problem of rear arrangement of penetration depth adjustment mechanism through the two sleeve structures of the external depth adjusting sleeve and the medium depth adjusting sleeve.

3. The present invention reasonably arranges the rotary mechanism, moving mechanism and rotary locating mechanism required for the penetration depth adjusting mechanism in the two sleeve structures with the reasonable design, ingenious conception, outstanding substantive characteristics and significant progress.

4. The invention is well-adapted, and it can not only be applied to the structure form of insert-plug connection between the cap and the cap holder through the plug-in port, but also to the structure form of threaded connection between the cap and the cap holder through the threaded port, and the structure form of the connection by the plug-in of cap and cap holder first and then through the rotary lock.

5. The invention has better process manufacturability, reliable operation and convenient use, and it further improves the usability of the lancing device, and plays a positive role in the improvement and development of the lancing device.

BRIEF DESCRIPTION OF THE DRAWINGS

FIG. 14 is the view of initial assembly state of an embodiment of lancing device of present invention;

FIG. 15 is the view of an embodiment of lancing device of present invention with the cap removed;

FIG. 16 is the view of an embodiment of lancing device of present invention with the lancet installed;

FIG. 17 is the view of an embodiment of lancing device of present invention with the lancet installed, pressed and loaded;

FIG. 18 is the view of an embodiment of lancing device of present invention with the lancet installed and loaded by the cocking handle;

FIG. 19 is the view of an embodiment of lancing device of present invention in the retracted state of the cocking handle under the reset spring for ejection pin;

FIG. 20 is the view of an embodiment of lancing device of present invention when the manual adjusting ring is rotated to a suitable setting and the press button is pressed;

FIG. 21 is the view of an embodiment of lancing device of present invention when the ejection pin is pushed by the ejection spring to be in the ejection state;

FIG. 24 is the view of an embodiment of lancing device of present invention when the ejection pin is reset;

FIG. 25 is the view of an embodiment of lancing device of present invention when the cap is removed and the cocking handle is pushed to unload the lancet;

In the above figures: 1. cap; 2. cap holder; 3. lancing end face; 4. connection port; 5. lancet; 6. ejection pin; 7. active impact face; 8. external depth adjusting sleeve; 9. medium depth adjusting sleeve; 10. manual adjusting ring; 11. rotary locating slot; 12. rotary locating block; 13. passive impact face; 14. spiral groove; 15. drive block; 16. inner lug; 17. shell; 18. limit slot; 19. division slot; 20. elastic bridge; 21. outer lug; 22. cocking handle; 23. press button; 24. safety plug; 25. clip; 26. locking plug for ejection pin; 27. unloading pin; 28. reset spring for ejection pin; 29. reset spring for unloading by cocking handle; 30. ejection spring; 31. lancet holder.

SPECIFIC EMBODIMENT

With reference to the accompanying drawings and embodiment, the present invention will be described in detail.

Embodiment: a lancing device with rear adjustment of penetration depth

Figure 1:
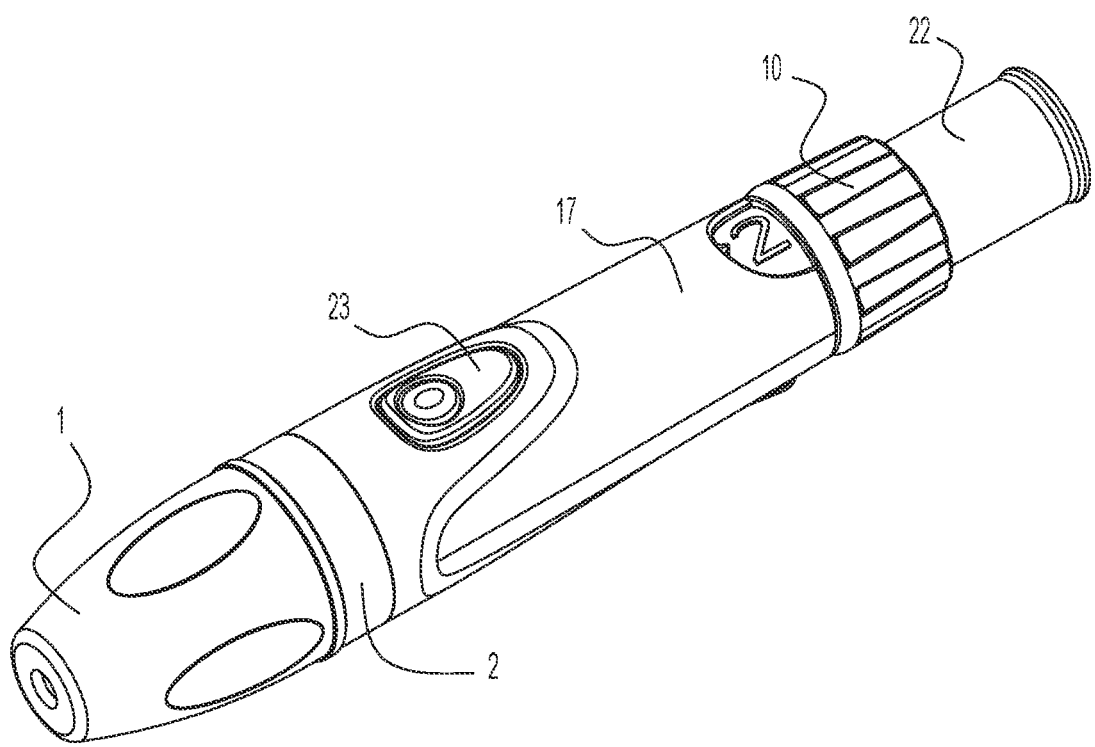
FIG. 1 is a perspective view of an embodiment of lancing device of present invention.
Figure 2:
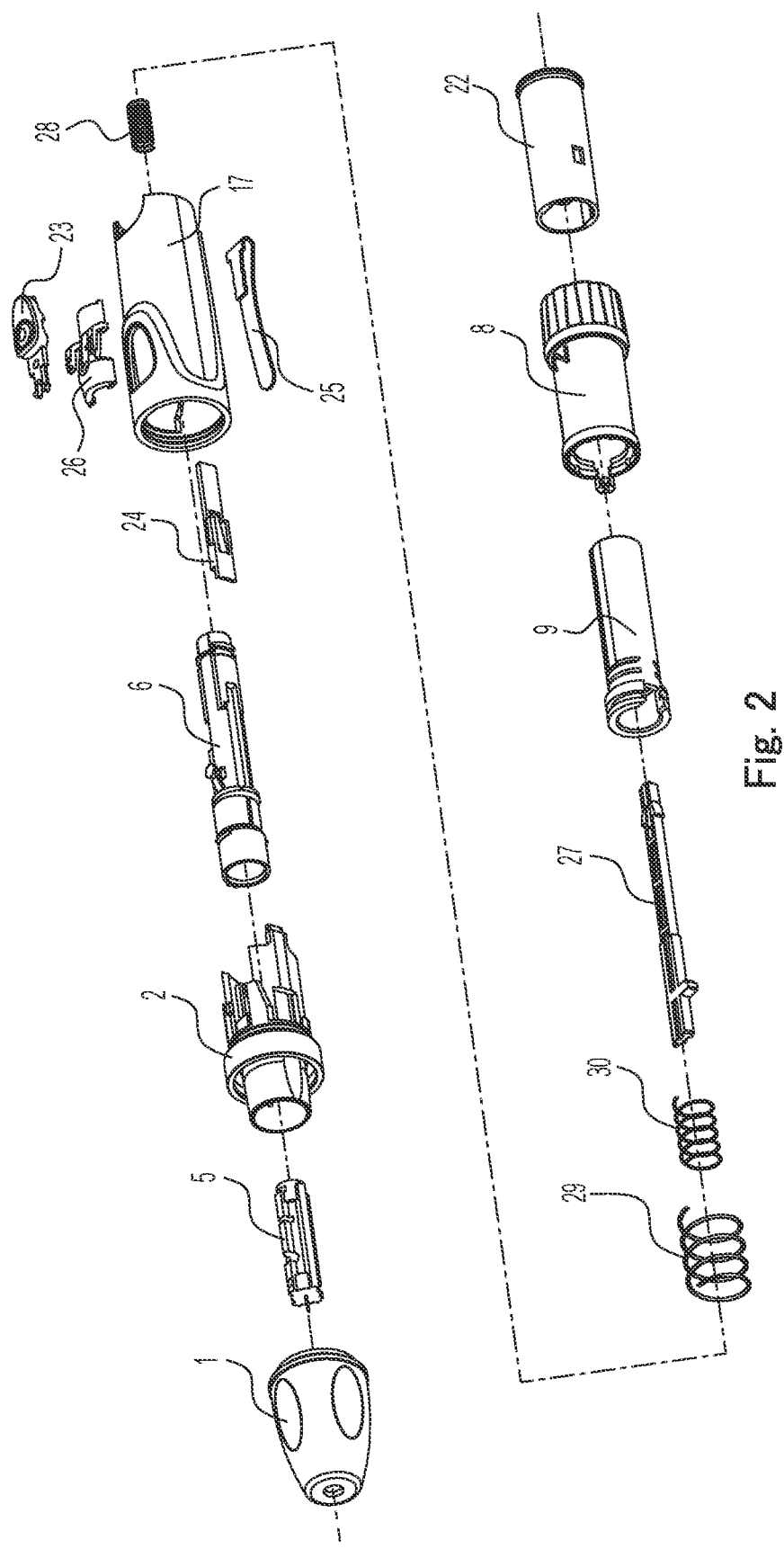
FIG. 2 is a exploded view of an embodiment of lancing device of present invention.
Figure 3:
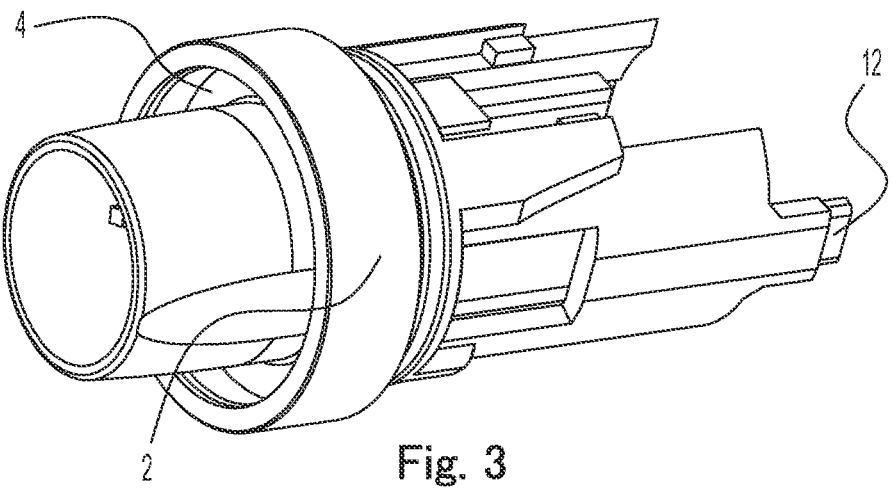
FIG. 3 is a perspective view of the cap holder of an embodiment of lancing device of present invention.
Figure 4:
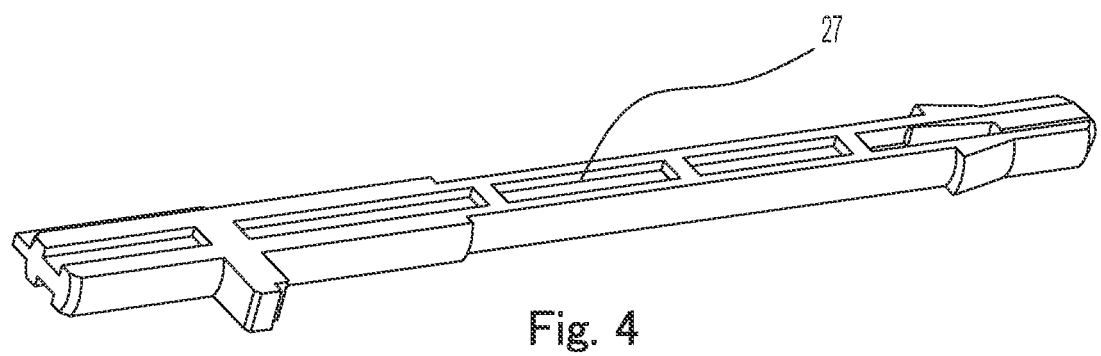
FIG. 4 is a perspective view of the unloading pin of an embodiment of lancing device of present invention.

As shown in FIG. 1~3, the lancing device comprises a cap 1, a cap holder 2, an ejection pin 6, a safety plug 24, a shell 7, a locking plug for ejection pin 26, a press button 23, a clip 25, a reset spring for ejection pin 28, a reset spring for unloading by cocking handle 29, an ejection spring 30, an unloading pin 27, a medium depth adjusting sleeve 9, an external depth adjusting sleeve 8 and a cocking handle 22 (see FIG. 2).

Figure 5:
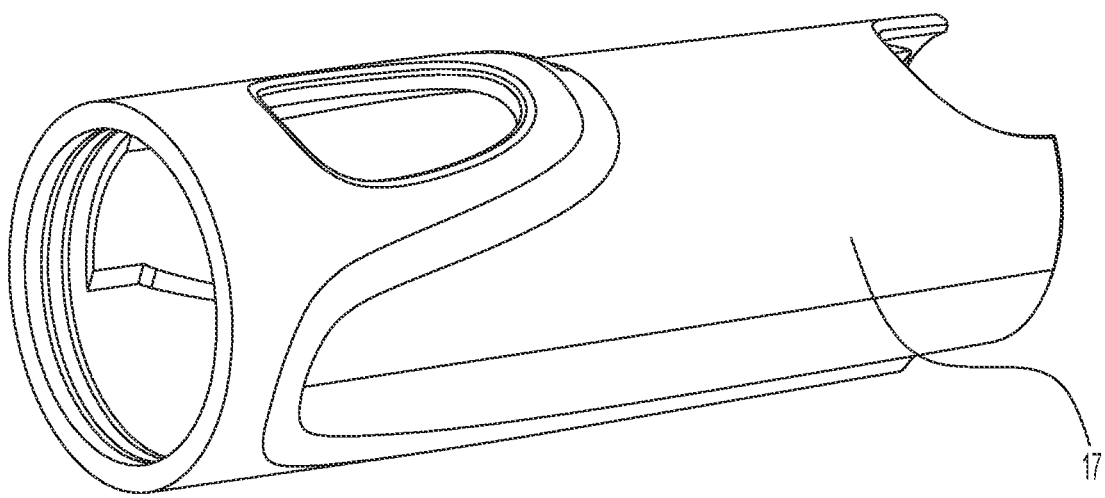
FIG. 5 is a perspective view of the shell of an embodiment of lancing device of present invention.
Figure 9:
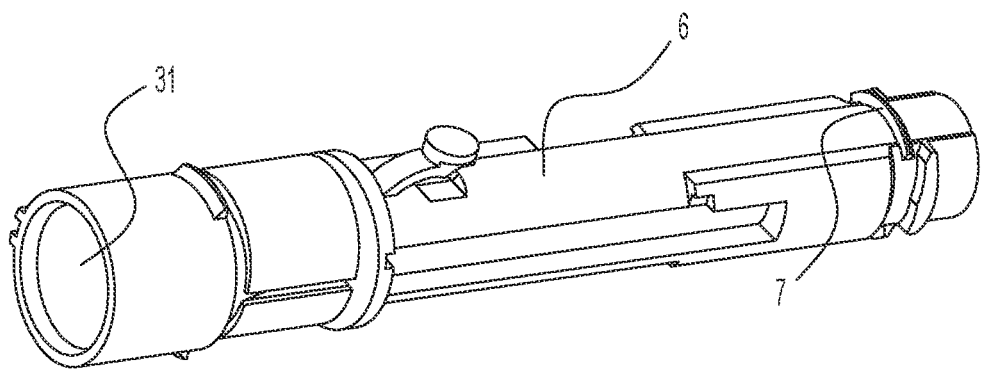
FIG. 9 is a perspective view of the ejection pin of an embodiment of lancing device of present invention.
Figure 10:
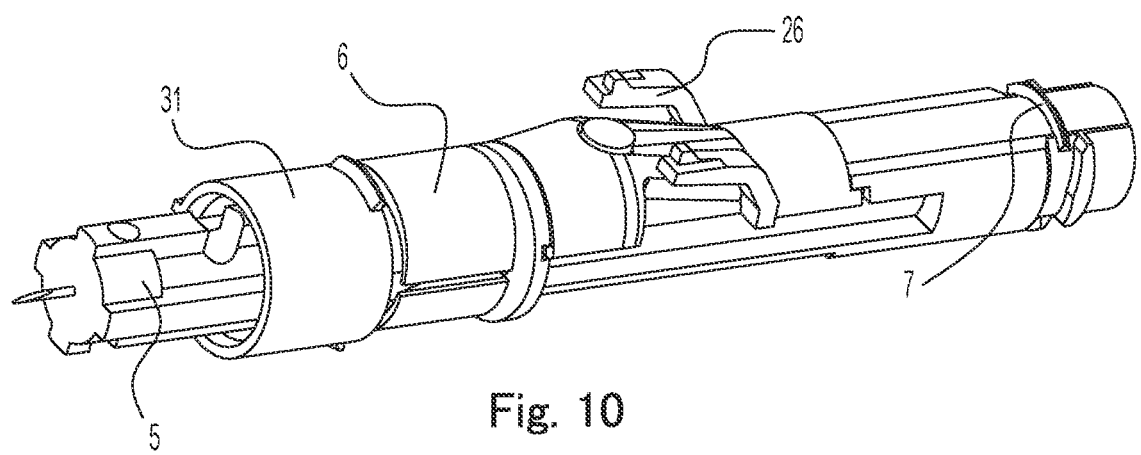
FIG. 10 is a perspective view of the assembly state of ejection pin, lancet and locking plug for ejection pin of an embodiment of lancing device of present invention.
Figure 11:
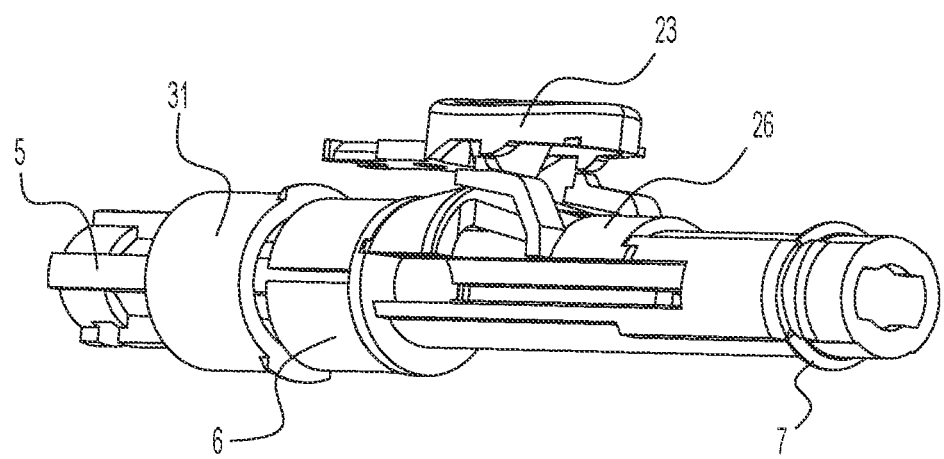
FIG. 11 is a perspective view of the assembly state of ejection pin, lancet, locking plug for ejection pin and press button of an embodiment of lancing device of present invention.
Figure 12:
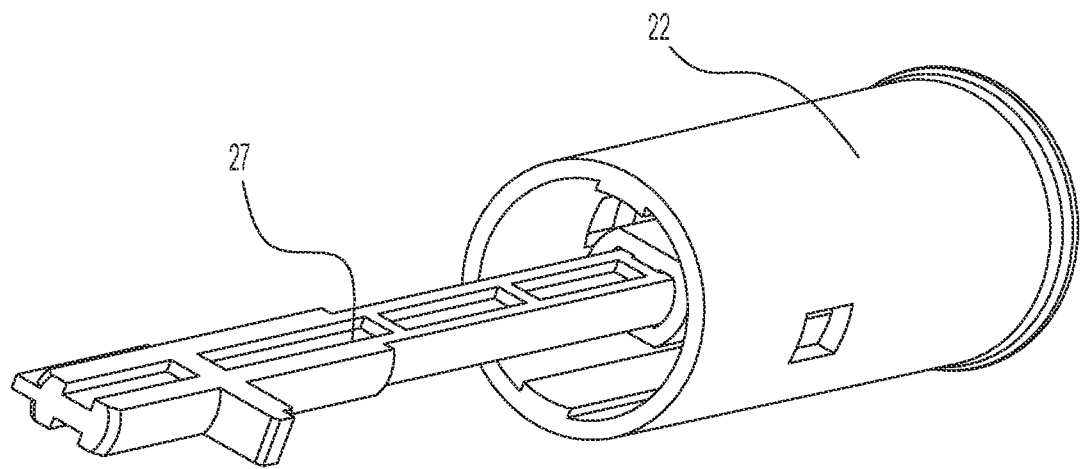
FIG. 12 is a perspective view of the assembly state of the unloading pin and cocking handle of an embodiment of lancing device of present invention.

The cap 1 is a sleeve type cap at the head of the lancing device, and the cap 1 is provided with a lancing end face 3 to contact the lancing site of human body at its front end. The cap holder 2 is the base used to connect and fit with the cap 1 at the front of the lancing device, and the cap 1 and the cap holder 2 are fit and connected through the connection port 4. In this embodiment, the connection port 4 is an insert-plug port (see FIG. 3), and the cap 1 and the cap holder 2 form the insert-plug connection through the insert-plug port. The ejection pin 6 is an ejection component capable of mounting a lancet 5, and the ejection pin 6 is provided with an active impact face 7. In this embodiment, the ejection pin 7 is provided with a lancet holder 31 at the head, used to install the lancet 6 and the active impact face 7 is arranged on the lateral face of the tail of the ejection pin 6 (see FIG. 9). The locking plug for ejection pin 26 is fitted on the ejection pin 6 (see FIG. 10). The ejection pin 6 fitted with the locking plug for ejection pin 26 cooperates with the press button 23 to form the locking and unlocking mechanism of the ejection pin 6 (see FIG. 11). In this embodiment, the ejection pin 6 and the locking plug for ejection pin 26 are the separate structures, but the invention is not limited to this and they can be designed to be an integrated structure (not shown in the figure). The shell 17 is the shell of the lancing device (see FIG. 5), and the shell 17 and the cap holder are connected in a fixed way, but the shell 17 and the cap holder 2 can be designed as an integrated structure. The safety plug 24 is fitted in a sliding channel on the cap holder 2 and it's used to prevent from unloading the lancet by mistake during use. Since the structure is not related to the rear adjustment of penetration depth of the invention, it will not be elaborated here. The cocking handle 22 is used for loading after the lancet 5 is installed and it's used to unload the lancet after use. The cocking handle 22 is connected with the unloading pin 27 in a fixed way (see FIG. 12).

Figure 6:
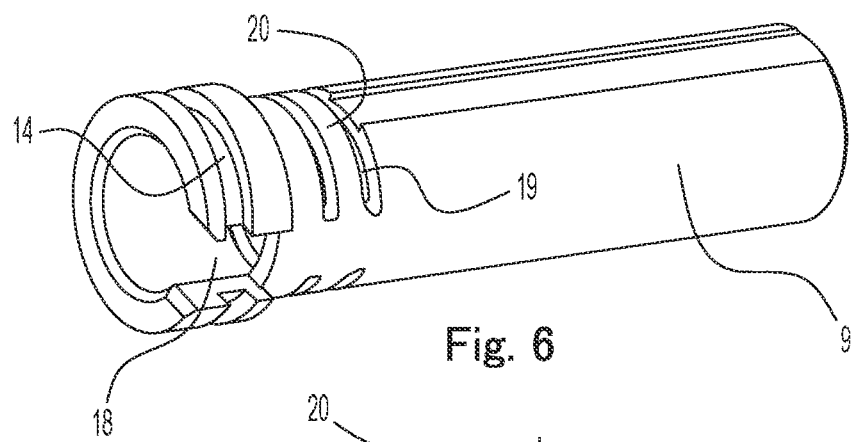
FIG. 6 is a perspective view of the medium depth adjusting sleeve of an embodiment of lancing device of present invention.
Figure 13:
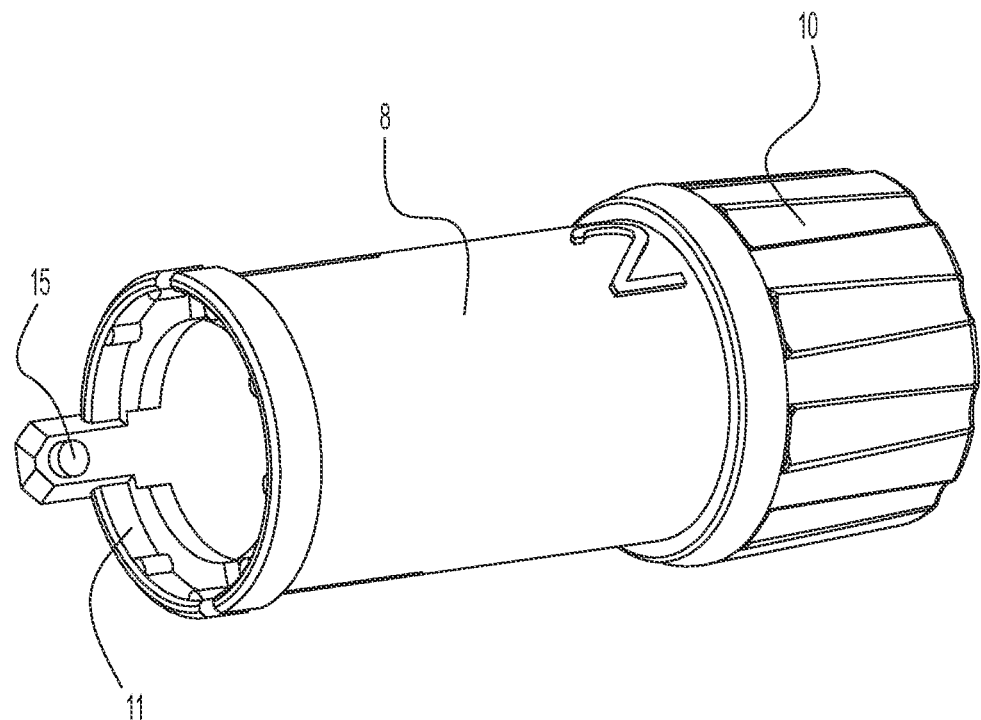
FIG. 13 is a perspective view of the external depth adjusting sleeve of an embodiment of lancing device of present invention.

The innovation of the present invention is to design a double sleeve type rear adjustment structure of penetration depth for a lancing device. The details are as follows:

The lancing device is provided with an external depth adjusting sleeve 8 (see FIG. 13) and a medium depth adjusting sleeve 9 (see FIG. 6). The main bodies of the external depth adjusting sleeve 8 and the medium depth adjusting sleeve 9 are sleeve structures. The ejection pin 6 is located in the medium depth adjusting sleeve 9 and the external depth adjusting sleeve 8 is sleeved outside the medium depth adjusting sleeve 9.

The external depth adjusting sleeve 8 is connected in the circumferential direction of the lancing device relative to the shell 17 in a rotational way and it's connected in the axial direction of the lancing device in a locating way. In this embodiment, specifically: the external depth adjusting sleeve 8 is provided with a circular recess at the outer edge (see FIG. 13) and the shell 17 is provided with a protruding rib at the inner edge, and the protruding rib cooperates with the circular recess. And they can be switched, that is, the external depth adjusting sleeve 8 is provided with a protruding rib at the outer edge and the shell 17 is provided with a circular recess at the inner edge. The external depth adjusting sleeve 8 is provided with a manual adjusting ring 10 and the manual adjusting ring 10 is a section of sleeve at the middle and rear part of the external depth adjusting sleeve 8 (see FIG. 13) and in the assembly state, the manual adjusting ring 10 is exposed at the middle outside or rear outside of the lancing device, so that the user can rotate and adjust manually. The external depth adjusting sleeve is is provided with a rotary locating slot 11 (see FIG. 13) and the cap holder is provided with a rotary locating block 12 (see FIG. 3), and the rotary locating slots 11 are several slots spaced on the circumferential direction of the lancing device, and the rotary locating blocks 12 are blocks configured for the corresponding rotary locating slots 11, and the matching between the rotary locating slots 11 and rotary locating blocks 12 forms a rotary locating mechanism of the external depth adjusting sleeve 8 in the circumferential direction of the lancing device relative to the shell 17. The positions of rotary locating slot 11 and rotary locating block 12 can be switched, that is, the external depth adjusting sleeve is provided with a rotary locating block 12 and the cap holder is provided with a rotary locating slot 11. Since the cap holder 2 and the shell 17 are connected in a fixed way in the assembly state, the rotary locating slot 11 or the rotary locating block 12 can be changed from being arranged on the cap holder 2 to being arranged on the shell 17 (as long as the structure allows).

Figure 7:
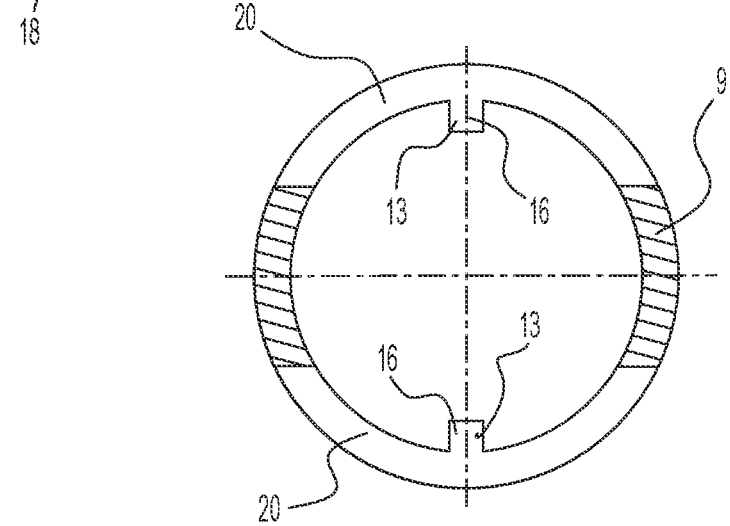
FIG. 7 is a sectional view of the elastic bridge of an embodiment of lancing device of present invention.

The medium depth adjusting sleeve 9 is connected in the circumferential direction of the lancing device relative to the shell 17 in a locating way and it's connected in the axial direction of the lancing device in a sliding way. In this embodiment, specifically: the medium depth adjusting sleeve 9 is provided with a limit slot 18 (see FIG. 6), and the cap holder 2 is provided with a stopper, and the limit slot 18 is arranged along the lancing device in the axial direction, and the limit slot 18 cooperates with the stopper. The positions of limit slot 18 and stopper can be switched, that is, the external depth adjusting sleeve 9 is provided with a stopper and the cap holder 2 is provided with a limit slot 18. Since the cap holder 2 and the shell 17 are connected in a fixed way in the assembly state, the limit slot 18 or the stopper can be changed from being arranged on the cap holder 2 to being arranged on the shell 17. The medium depth adjusting sleeve 9 is provided with a passive impact face 13 relative to the active impact face 7 (see FIG. 7). The medium depth adjusting sleeve 9 is provided with a spiral groove 14 (see FIG. 6) and the external depth adjusting sleeve 8 is provided with a drive block 15 (see FIG. 13), and the drive block 15 is a block configured for the corresponding spiral groove 14, and the matching of the spiral groove 14 and the drive block 15 forms a moving mechanism of the medium depth adjusting sleeve 9 in the axial direction of the lancing device relative to the shell 17. The positions of spiral groove 14 and drive block 15 can be switched, that is, the medium depth adjusting sleeve 9 is provided with a drive block 15 and the external depth adjusting sleeve 8 is provided with a spiral groove 14.

The medium depth adjusting sleeve 9 is a tubular member, and the main body structure of this tubular member is a round tube (see FIG. 6). The tubular member is provided with at least two pairs of division slots 19 at its outer edge along the transverse direction of the tubular body (see FIG. 6), and each pair of division slots 19 is formed by the two slots spaced in the axial direction of the tubular body, and all pairs of division slots 19 are spaced along the circumferential direction at the outer edge of the medium depth adjusting sleeve 9, and the opening of the slots in the circumferential direction at the outer edge of the medium depth adjusting sleeve 9 is less than 180 degrees and the slots are on the tube walls through the medium depth adjusting sleeve 9 in the radial direction of the tubular body, and each pair of division slots 19 isolates the tube wall in the middle to be an elastic bridge 20, and the two ends of the elastic bridge 20 are integrated with the medium depth adjusting sleeve 9, the arch of the elastic bridge 20 is independent relative to the medium depth adjusting sleeve 9 and the passive impact face 13 is arranged on the arch or the arch extension, and it's on the lateral side where the arch or the arch extension is against the active impact face 7 to form the buffer structure of elastic bridge. In this embodiment, the arch extension is an inner lug 16 extending inward from the inner side of the arch (see FIG. 7) and the passive impact face 13 is the lateral face where the inner lug 16 is against the active impact face 7, so the active impact face 7 cooperates with the passive impact face 13 in the inner side of the medium depth adjusting sleeve 9 in an impact way.

In order to better understand the relative position and relationship among the components in the invention, the lancing device of the invention is described with the use state as follows:

1. Initial Assembly State

FIG. 14 is the view of initial assembly state of an embodiment of lancing device of present invention. The relative position and relationship among the components in the initial assembly state can be seen from FIG. 14.

2. State with the Cap Removed

FIG. 15 is the view of an embodiment of lancing device of present invention with the cap removed. In the state with the cap removed, the cap 1 is removed, and the relative position and relationship among the other components is the same as that in FIG. 14.

3. State of Lancet Installed

FIG. 16 is the view of an embodiment of lancing device of present invention with the lancet installed. In the state with the lancet installed, the lancet 5 is inserted into the lancet holder 31 of the ejection pin 6.

4.1 State of Lancet Loaded

FIG. 17 is the view of an embodiment of lancing device of present invention with the lancet installed, pressed and loaded. In this state, it's only necessary to directly press the lancet 5 in the direction pointed by the arrow in FIG. 7, and the ejection pin 6 compresses the ejection spring 30, while the ejection pin 6 is locked on the press button 23 through the locking plug for ejection pin 26 and finally cover the cap 1.

4.2 State of Lancet Loaded by the Cocking Handle

FIG. 18 is the view of an embodiment of lancing device of present invention with the lancet installed and loaded by the cocking handle. In this state, if the method of directly pressing the lancet 5 for loading is not used, it's possible to cover the cap 1 first and then pull the cocking handle 22 backward, and the ejection pin 6 compresses the ejection spring 30, while the ejection pin 6 is locked on the press button 23 through the locking plug for ejection pin 26.

FIG. 19 is the view of an embodiment of lancing device of present invention in the retracted state of the cocking handle under the reset spring for ejection pin 28. At this point, the loading of the cocking handle is completed.

5. State of Adjusting the Penetration Depth

The adjustment of penetration depth could be carried out in this state and it can be adjusted in advance, and it shall be adjusted before the lancing in any case. The method of adjustment of penetration depth is: rotate the manual adjusting ring 10 on the external depth adjusting sleeve 8, and the external depth adjusting sleeve 8 drives the medium depth adjusting sleeve 9 to move axially relative to the shell 17 of the lancing device through the matching of the drive block 15 and the spiral groove 14, so as to change the distance between the lancing end face 3 and the passive impact face 13 in the axial direction of the lancing device, so as to adjust the penetration depth of the needle tip.

6. State of Pressing the Press Button

Figure 22:
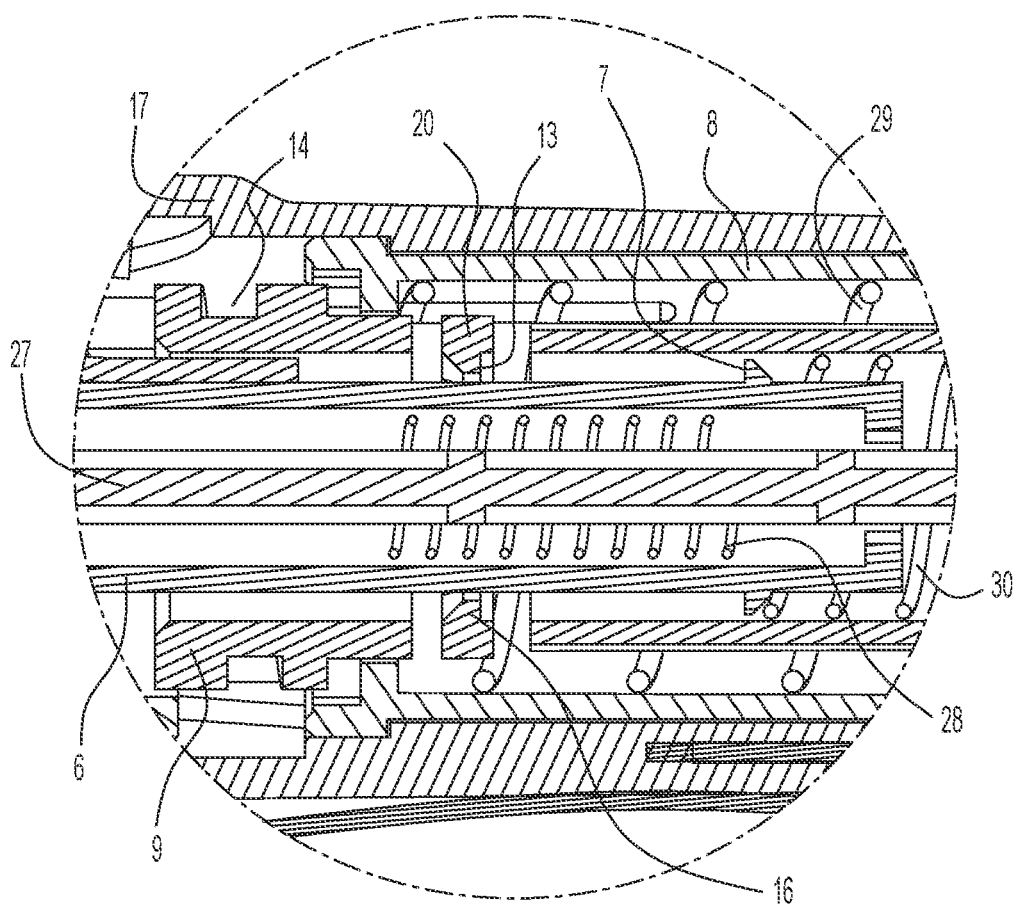
FIG. 22 is the enlarged view of area A in FIG. 20.

FIG. 20 is the view of an embodiment of lancing device of present invention when the manual adjusting ring 10 is rotated to a suitable setting and the press button 23 is pressed. FIG. 22 is the enlarged view of area A in FIG. 20. In this state, the press button 23 forces the ejection pin 6 and locking plug for ejection pin 26 to unhook.

7. State of Ejection of Ejection Pin and Lancet

Figure 23:
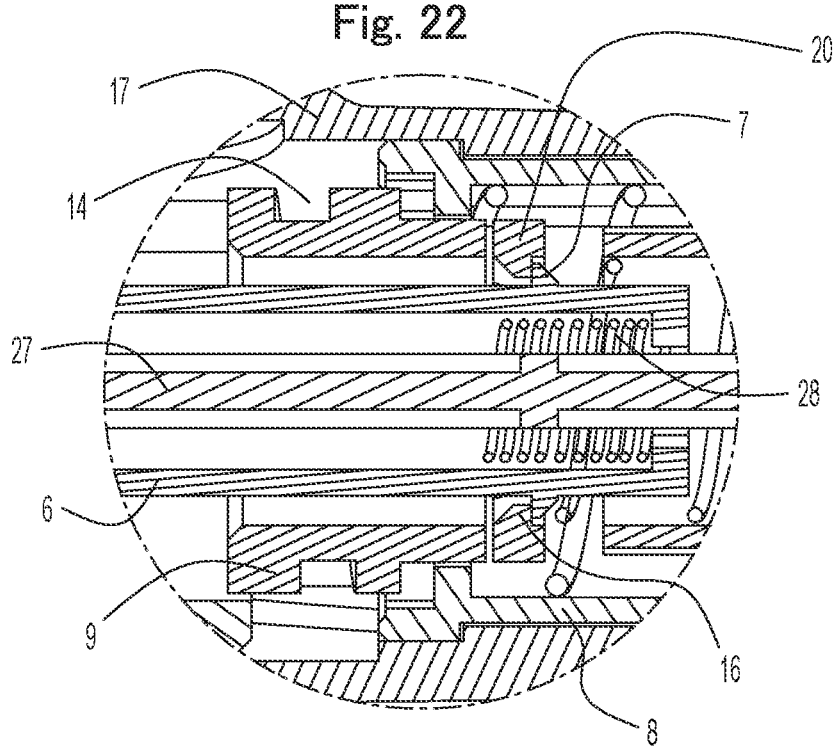
FIG. 23 is the enlarged view of area B in FIG. 21.

FIG. 21 is the view of an embodiment of lancing device of present invention when the ejection pin 6 is pushed by the ejection spring 30 to be in the ejection state. FIG. 23 is the enlarged view of area B in FIG. 21. In this state, the ejection spring 30 pushes the ejection pin 6 and lancet 5 to eject for puncturing.

8. State of Resetting Ejection Pin

FIG. 24 is the view of an embodiment of lancing device of present invention when the ejection pin 6 is reset. In this state, the ejection pin 6 is reset to the normal position in the axial direction of the lancing device under the action of the reset spring for ejection pin 28 and ejection spring 30.

9. State of Lancet Unloaded

FIG. 25 is the view of an embodiment of lancing device of present invention when the cap 1 is removed and the cocking handle 22 is pushed to unload the lancet 5; In this state, push the cocking handle 22 in the direction pointed by the arrow in the figure to force the lancet 5 to be unloaded from lancet holder 31 of the ejection pin 6, while the reset spring for unloading by cocking handle 29 is compressed.

10. State of Restoring the Initial State

Figure 26:
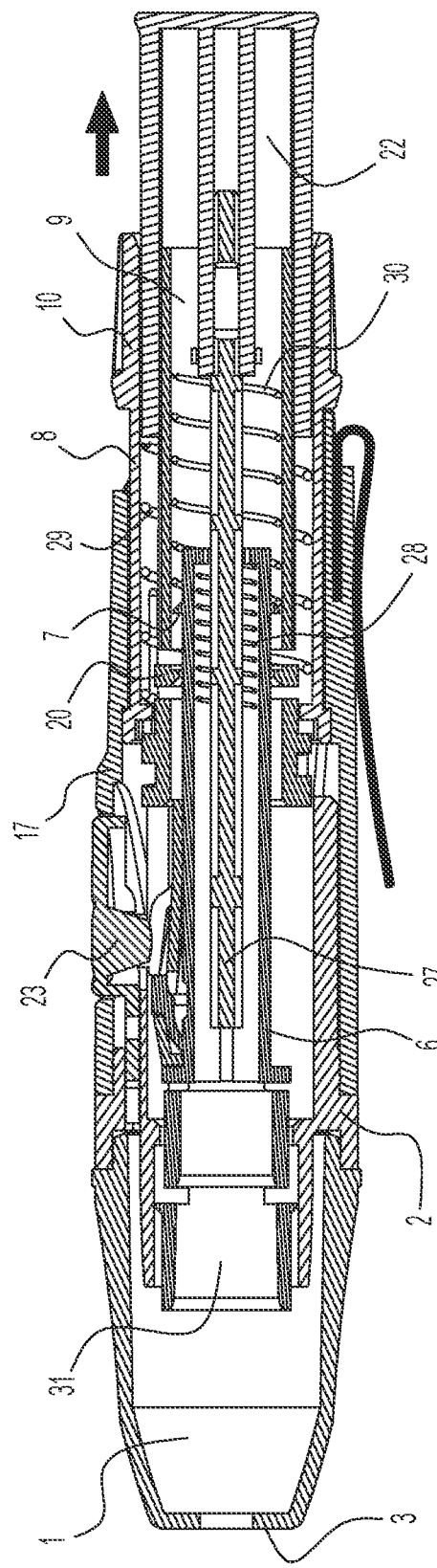
FIG. 26 is the view of an embodiment of lancing device of present invention when it restores the initial state.

FIG. 26 is the view of an embodiment of lancing device of present invention when it restores the initial state. In this state, the cocking handle 22 is reset under the action of the reset spring for unloading by cocking handle 29, and then cover the cap 1 to restore the initial assembly state.

Figure 8:
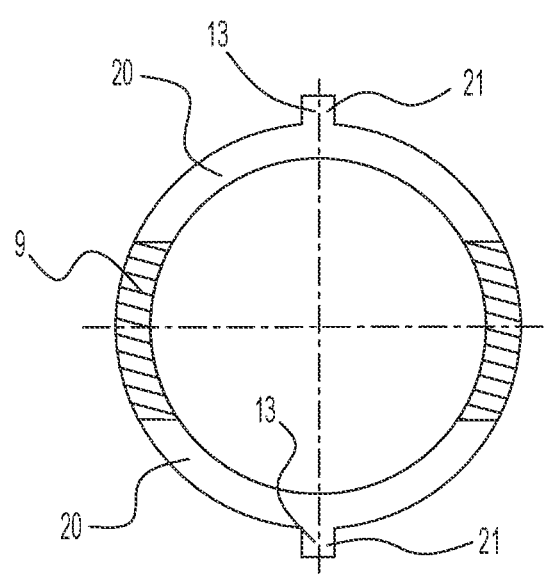
FIG. 8 is a sectional view of another elastic bridge of an embodiment of lancing device of present invention.

About the above-mentioned embodiments, the possible changes of present invention are described as follows:

1. In the above embodiment, the passive impact face 13 is arranged on the inner lug 16 extending inward from the inner side of arch of the elastic bridge 20 of the medium depth adjusting sleeve 9 (see FIG. 7). The present invention is not limited to this, and the passive impact face 13 can also be arranged on the inner lug 22 extending outward from the outer side of the arch of the elastic bridge 20 (see FIG. 8) and the passive impact face 13 is the lateral face where the outer lug 22 is against the active impact face 7, so the active impact face 7 cooperates with the passive impact face 13 in the outer side of the medium depth adjusting sleeve 9 in an impact way.
2. In the above embodiment, the passive impact face 13 is arranged on the elastic bridge 20 of the medium depth adjusting sleeve 9 to form the buffer structure of elastic bridge. The present invention is not limited to this, and the buffer structure of elastic bridge is not applied, that is, the medium depth adjusting sleeve 9 is provided with an inner lug 16 on the inner wall, and the passive impact face 13 is the end face of the inner lug 16 against the active impact face 7. The active impact face 7 is arranged on the side of the ejection pin 6 or the lancet 5 corresponding to the motion path of the passive impact face 13.
3. In the above embodiment, the active impact face 7 is arranged at the lateral face of the tail of the ejection pin 6. The present invention is not limited to this, and the active impact face 7 can be designed on the lancet 5.
4. In the above embodiment, the medium depth adjusting sleeve 9 is a tubular member, and the main body structure of this tubular member is a round tube (see FIG. 6). The present invention is not limited to this, and besides the round tube, the section shape of the medium depth adjusting sleeve 9 can also be rectangle, triangle, polygonal and special shape, etc., and it can be square tube, rectangular tube, triangle tube and polygonal tube.
5. In the above embodiment, the connection port 4 is an insert-plug port (see FIG. 3). The present invention is not limited to this, and the connection port 4 can be a threaded port, and the cap 1 and the cap holder 2 form a threaded connection through the threaded port. The connection port 4 can also be an insert-plug locking port, and the cap 1 and the cap holder 2 form an insert-plug locking connection through the insert-plug locking port.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A lancing device with rear adjustment of penetration depth comprising:
a cap;
a cap holder;
an ejection pin; and
an active impact face; and
a shell, wherein:
the cap is a sleeve type cap at a head of the lancing device, and the cap is provided with a lancing end face configured to contact a lancing site of a human body;
the cap holder is configured to connect and fit with the cap at a front end of the lancing device, and the cap and the cap holder are configured to fit and connect through a connection port;
the ejection pin is an ejection component configured to mount a lancet;
the shell and the cap holder are connected in a fixed manner;
the lancing device includes an external depth adjusting sleeve and a medium depth adjusting sleeve;
the ejection pin is located in the medium depth adjusting sleeve and the medium depth adjusting sleeve is provided in the external depth adjusting sleeve;
the external depth adjusting sleeve is connected in a circumferential direction of the lancing device relative to the shell in a rotational way and the external depth adjusting sleeve is connected in an axial direction of the lancing device in a locating way;

the external depth adjusting sleeve is provided with a manual adjusting ring, and the manual adjusting ring is a sleeve that extends from a middle of the external depth adjusting sleeve and to a rear of the external depth adjusting sleeve, and when assembled, the manual adjusting ring is exposed so that a user can rotate the manual adjusting ring;

between the external depth adjusting sleeve and one of the cap holder and the shell, the external depth adjusting sleeve is provided with a plurality of rotary locating slots, and the one of the cap holder and the shell is provided with a rotary locating block, the plurality of rotary locating slots are spaced along a circumferential direction of the lancing device, the rotary locating block is configured to correspond to one of the plurality of rotary locating slot to form a rotary locating mechanism in the circumferential direction of the lancing device relative to the shell;

the medium depth adjusting sleeve is connected in the circumferential direction of the lancing device relative to the shell in a locating way and connected in the axial direction of the lancing device in a sliding way;

the medium depth adjusting sleeve is provided with a passive impact face configured to interact with the active impact face;

one of the medium depth adjusting sleeve and the external depth adjusting sleeve is provided with a spiral groove and one of the other of the medium depth adjusting sleeve and the external depth adjusting sleeve is provided with a drive block, and the drive block is a block configured for a corresponding spiral groove, and aligning the spiral groove and the drive block forms a moving mechanism of the medium depth adjusting sleeve in the axial direction of the lancing device relative to the shell;

when assembled, the manual adjusting ring on the external depth adjusting sleeve is configured to rotate to drive the medium depth adjusting sleeve to move axially relative to the shell of the lancing device, so as to change a distance between the lancing end face and the passive impact face in the axial direction of the lancing device, so as to adjust the penetration depth of a needle tip;

the medium depth adjusting sleeve is a tubular member;

the tubular member is provided with at least two pairs of division slots at an outer edge of the tubular member along a circumferential direction of a tubular body;

each pair of division slots is formed by the two slots spaced in an axial direction of the tubular body;

all pairs of division slots are spaced along the circumferential direction at the outer edge of the medium depth adjusting sleeve, and an opening of the slots in the circumferential direction at the outer edge of the medium depth adjusting sleeve is less than 180 degrees and the slots extend through a wall of the medium depth adjusting sleeve in a radial direction of the tubular body;

each pair of division slots isolates a tube wall in the middle to be an elastic bridge;

the two ends of the elastic bridge are integrated with the medium depth adjusting sleeve, an arch of the elastic bridge is separate from the medium depth adjusting sleeve; and the passive impact face is arranged on the arch or an arch extension of the elastic bridge and is configured to impact the active impact face.

2. The lancing device according to the claim 1, wherein:
the medium depth adjusting sleeve includes an inner lug on an inner wall of the medium depth adjusting sleeve, and the passive impact face is an end face of the inner lug configured to contact the active impact face; and
the active impact face is arranged on one of a side of the ejection pin and the lancet corresponding to a motion path of the passive impact face.

3. The lancing device according to the claim 1, wherein:
the arch extension is an inner lug extending inward from an inner side of the arch and the passive impact face is the inner lug and configured to contact the active impact face.

4. The lancing device according to the claim 1, wherein:
the arch extension is an outer lug extending outward from an outer side of the arch and the passive impact face is the outer lug and is configured to contact the active impact face.

5. The lancing device according to the claim 1, wherein:
the external depth adjusting sleeve is connected in the circumferential direction of the lancing device relative to the shell in a rotational way and the external depth adjusting sleeve is connected in the axial direction of the lancing device in a locating way, and the external depth adjusting sleeve includes an outer edge provided with a circular recess and an inner edge of the shell is provided with a protruding rib, such that the protruding rib cooperates with the circular recess.

6. The lancing device according to the claim 1, wherein:
the medium depth adjusting sleeve is connected in the circumferential direction of the lancing device relative to the shell in a locating way and connected in the axial direction of the lancing device in a sliding way, and the medium adjusting sleeve includes a limit slot and one of the shell and the cap holder is configured to include a stopper, and the limit slot is arranged along the lancing device in the axial direction, and the limit slot is configured to receive the stopper.

7. The lancing device according to the claim 1, wherein:
the connection port is an insert-plug port, and the cap and the cap holder form an insert-plug connection through the insert-plug port.

8. The lancing device according to the claim 1, wherein:
the connection port is a threaded port, and the cap and the cap holder form a threaded connection through the threaded port.

9. The lancing device according to the claim 1, wherein:
the connection port is an insert-plug locking port, and the cap and the cap holder are configured to form an insert-plug locking connection through the insert-plug locking port.

* * * * *